United States Patent [19]
Farin et al.

[11] 4,137,919
[45] Feb. 6, 1979

[54] ELECTROMEDICAL CLIP STRUCTURE

[75] Inventors: Günter Farin, Tübingen Hirschau; Günther Posselt, Neuenstetten, both of Fed. Rep. of Germany

[73] Assignee: Erbe Elektromedizin KG, Tübingen, Fed. Rep. of Germany

[21] Appl. No.: 828,979

[22] Filed: Aug. 29, 1977

[30] Foreign Application Priority Data

Sep. 4, 1976 [DE] Fed. Rep. of Germany ....... 2639956

[51] Int. Cl.$^2$ .................. A61B 17/36; A61N 3/06
[52] U.S. Cl. .................. 128/303.17; 219/234
[58] Field of Search .......... 128/303.17, 303.1, 303.13, 128/303.14, 303.15, 303.16, 303.18, 354, 405; 219/234, 233, 230, 90

[56] References Cited
U.S. PATENT DOCUMENTS

| | | | |
|---|---|---|---|
| 1,071,978 | 9/1913 | White | 128/303.13 |
| 2,012,937 | 9/1935 | Bevoy | 128/303.14 X |
| 2,623,152 | 12/1952 | Ammon | 219/234 |
| 2,636,971 | 4/1953 | Delbrook | 219/233 |
| 3,643,663 | 2/1972 | Gutter | 128/303.17 |
| 3,685,518 | 8/1972 | Beuerle et al. | 128/303.17 |
| 4,041,952 | 8/1977 | Morrison, Jr. et al. | 128/303.13 |

FOREIGN PATENT DOCUMENTS 138672  8/1961  U.S.S.R. ............... 128/303.17

*Primary Examiner*—Lee S. Cohen
*Attorney, Agent, or Firm*—Flynn & Frishauf

[57] ABSTRACT

The base of a clip or forceps for application of high-frequency electricity for coagulation of living tissues provides mechanical securing of the electrodes to each other by means of a dovetail tongue and groove engagement with an intervening insulation layer of material hardened after injection between the jaws or branches of the clip. A contact socket can simply be applied over the surface of the base of the clip, so that the device is easily handled by the surgeon, while at the same time the security of the mechanical fastening at the base of the clip is not subject to impairment by repeated sterilization at 134° C.

1 Claim, 3 Drawing Figures

ELECTROMEDICAL CLIP STRUCTURE

The present invention relates to a contact forceps or clip for use in producing coagulation of body tissues in high-frequency electric surgery, sometimes known as bipolar coagulation. The jaws of the clip or forcep act as electrodes for applying the high-frequency electric current that produces the coagulation of biological tissue and the connections to the high-frequency circuit are usually made at the end of the clip or forceps where the two prongs are joined, in order to leave the rest of the device free to be applied as the surgeon sees fit. The invention relates particularly to forceps or clips in which, where the branches or jaws of the device are joined together, they are joined together by a layer of electric insulating material that is usually provided as an insulating adhesive.

A difficulty has been found in the manufacture of such clips or forceps in the portion of the device where the two arms or jaws are mechanically joined together, where on the one hand mechanical stability must be provided and, on the other hand, also electric insulation between the two electrodes. The problem is made more difficult because such forceps or clips must be sterilized at 134° C., which imposes additional requirements relating particularly to the insulation material of the device.

If the facing surfaces of the branches or jaws of the device that must be held together by adhesive are plane, the adhesive layer breaks off relatively easily. It has therefore already been proposed to provide profile projections on the oppositely lying intermediate surfaces of the branches or jaws, in order to increase the solidity of the adhesive joint. Since nevertheless the bending forces exerted in a direction perpendicular to the longitudinal axis of the forceps or clip must be resisted by the adhesive layer, the solidity of the connection is dependent upon the tension resistance or stripping resistance of the adhesive. After repeated sterilization of such forceps or clips at 134° C., the solidity tends to yield, so that the connection eventually tears apart.

To obtain a sufficient solidity of the joint, it is also known to encase the branch or jaw ends that are secured together by adhesive in a ring or a piece of tubing, so that a satisfactory mechanical solidity can be provided. Such forceps or clips have the disadvantage that as the result of the encasing by a piece of tubing, a relatively large weight is produced at the end of the device, so that the handling of the device by the surgeon is disadvantageously affected.

It is therefore an object of the present invention to provide a forceps or clip in which an increased mechanical stability of the electricallly insulating connection is effected without the necessity of a casing or of similar means by which the handling of the device, or its convenient connection possibilities to the lugs or plug of the electrical cable connection, might be in any way limited.

SUMMARY OF THE INVENTION

Briefly, a longitudinal ridge on one of the conducting jaws or branches of the forceps or clip is provided that has a cross-sectional profile of dovetail shape and a corresponding dovetail groove is provided in the other into which the ridge can be slid, allowing spacing for a layer of insulating material, preferably adhesive material, therebetween.

By such a keyed connection, after the fashion of a dovetail tongue and groove joint, only movement of the two branches or jaws in the longitudinal direction of the dovetail groove is possible. Since there is no loading in this direction in the intended use of the device, no mechanical loading of the insulating layer results during use of the device. As against the use of a surrounding casing or shell, there is the substantial advantage, in the construction according to the invention, that no special plug devices are necessary for connection of the high-frequency current circuit, since current-applying leads can be fastened directly to the branches or jaws of the forceps or clip or a connector of a supply cable can be fitted to the outer form of the forceps or clip end.

The invention is further described by way of specific example with reference to the annexed drawing, in which.

Figure 1:
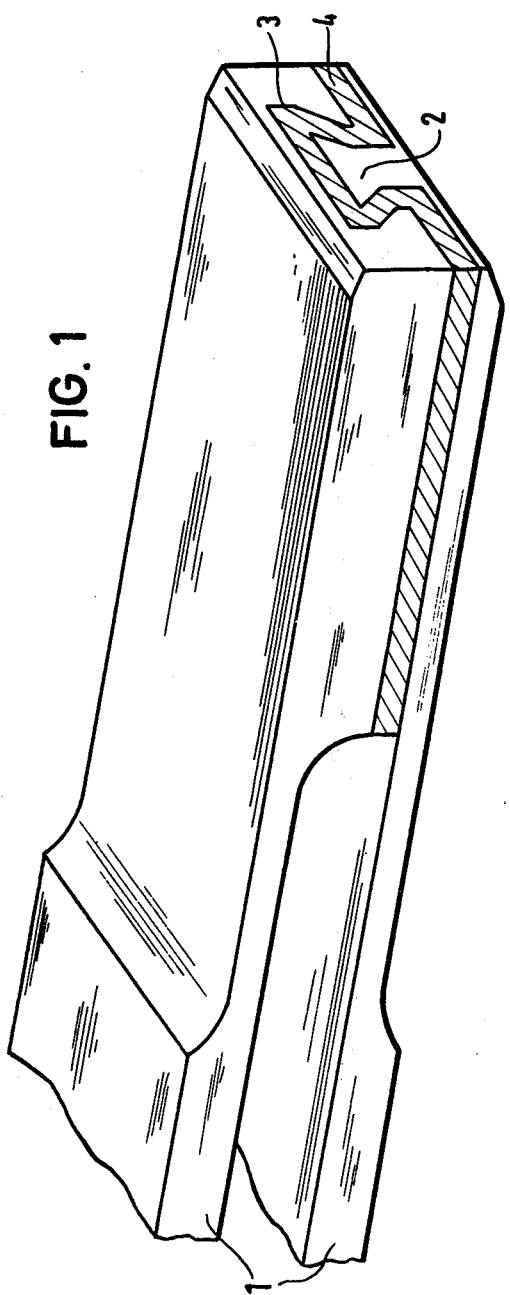
FIG. 1 is a perspective view of the connection end of a forceps or clip in accordance with the invention.

In FIG. 1, only the connection end of a clip or forceps is shown, the separated ends which apply the high-frequency current to the tissues being shown broken away at the left. Where the two branches or jaws of the device come together, as shown in the righthand portion of FIG. 1, the lower jaw or branch has a longitudinal ridge of dovetail profile 2 and the upper one has a longitudinal groove 3 likewise of dovetail profile, but of somewhat greater dimensions, so that there is room in between for an adhesive layer 4 of insulating material. Although the dovetail profile has what might be called a triangular upper end, a similar rectangular profile could be provided, more or less in the form of a T profile, to the same effect, which may be regarded as a rectangular version of a dovetail keyway or tongue-and-groove joint profile. Between the tongue and the groove, there is plenty of space for an insulating adhesive layer 4 which is required to resist only the forces arising in the longitudinal direction aligned with the groove and ridge, because forces in all other directions tending to pull the two metal parts apart are resisted by the dovetail engagement and the adhesive layer is stressed only in compression and not substantially in shear. The adhesive layer 4 can be provided in manufacture by squirting in a synthetic material that is subsequently to be hardened, as in injection molding, after the metal pieces 1 have been temporarily secured in the correct position for the injection of the synthetic resin to be hardened. The insulating material is referred to as an adhesive, because it is preferably one which has a good surface bonding with the metal of the jaws or branches 1 of the forceps or clip. Naturally, in the case of injection of the material, a mold will be provided to confine the insulating layer to where the surfaces of the pieces 1 are close together, and the rest of the mold cavity will be made of a material or provided with a coating to which the insulating material does not stick.

Since when the branches or jaws of such a forceps or clip are spread apart the insulating layer of the device is not stressed in shear along the longitudinal axis of the jaws, but is stressed only in compression, a synthetic material such as a glass fiber reinforced epoxy resin can be used without any difficulties.

Figure 3:
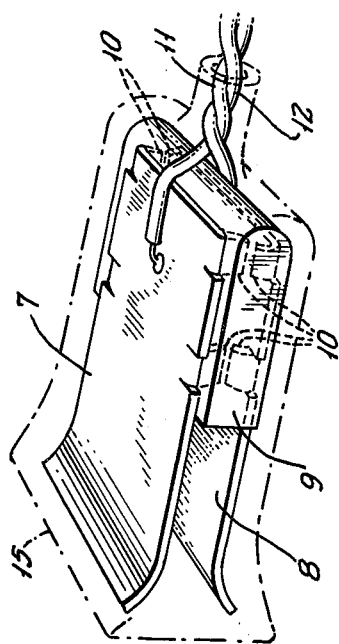
FIG. 3 is a diagram of a socket connector for supplying high-frequency current to the jaws or branches of the device shown in FIGS. 1 and 2.
Figure 2:
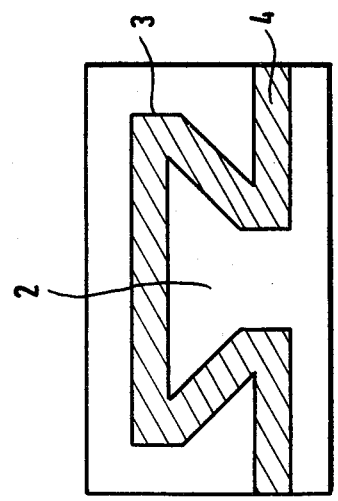
FIG. 2 is a cross-section in the plane II—II of FIG. 1.

FIG. 3 shows a simple form of connector that can be slipped on over the end of the device of FIG. 1 to provide the connections. The device shown in FIG. 3 is on a smaller scale and has a pair of flat springy contact leaves 7 and 8 molded into an insulating block 9 with the help of inwardly projecting tongues 10 shown by broken lines. Wires 11 and 12 that are insulated, except at their ends, are soldered to the leaf contacts 7 and 8. A flexible and relatively loose synthetic casing 15 is provided around the outside of the connector, so that unwanted connections to the high-frequency electric circuit will not be made. The connecting cable, of course, can be a coaxial cable instead of the twisted pair 11,12.

Although the invention has been described with reference to a particular illustrative embodiment, it is evident that variations may be made within the inventive concept.

We claim:

1. In a clip or forceps for application of high-frequency current to biological tissues for coagulation of tissues for surgical purposes, comprising a pair of jaws or branches made at least in part of electrically conducting material having forward and rear ends, the rear ends being mechanically fastened together and insulated from each other, the improvement which consists in that the rear end of one of the jaws or branches has a longitudinal ridge of essentially dovetail profile and the rear end of the other has a longitudinal groove of similar dovetail profile of sufficiently larger dimensions to accomodate an intervening layer, the ridge being positioned within the groove to achieve the mechanical fastening, and a layer of insulating material being provided between the opposed surfaces of the two jaws or branches in the region of their mechanical fastening, occupying at least in part the intervening space between the dovetail profile ridge and the dovetail profile groove.

* * * * *